United States Patent
Suda et al.

(10) Patent No.: US 8,242,222 B2
(45) Date of Patent: Aug. 14, 2012

(54) POLYSILOXANE, ACRYLIC COMPOUND AND VINYLIC COMPOUND

(75) Inventors: Yukimitsu Suda, Kanagawa (JP); Kazuyuki Miyazawa, Kanagawa (JP)

(73) Assignee: Shiseido Company, Ltd., Tokyo (JP)

(*) Notice: Subject to any disclaimer, the term of this patent is extended or adjusted under 35 U.S.C. 154(b) by 114 days.

(21) Appl. No.: 12/934,682

(22) PCT Filed: Mar. 31, 2009

(86) PCT No.: PCT/JP2009/056657
§ 371 (c)(1), (2), (4) Date: Sep. 27, 2010

(87) PCT Pub. No.: WO2009/123191
PCT Pub. Date: Oct. 8, 2009

(65) Prior Publication Data
US 2011/0040053 A1    Feb. 17, 2011

(30) Foreign Application Priority Data

Mar. 31, 2008 (JP) ................. 2008-092762
Mar. 31, 2008 (JP) ................. 2008-092763
Mar. 31, 2008 (JP) ................. 2008-092764

(51) Int. Cl.
*C08F 120/10* (2006.01)
*C08G 77/395* (2006.01)
*C08G 77/04* (2006.01)
*C08G 77/26* (2006.01)

(52) U.S. Cl. ............... 526/193; 528/28; 528/38
(58) Field of Classification Search .......... 526/193; 528/28, 38
See application file for complete search history.

(56) References Cited

U.S. PATENT DOCUMENTS

| | | | |
|---|---|---|---|
| 4,348,329 | A | 9/1982 | Chapman |
| 5,453,467 | A | 9/1995 | Bamford et al. |
| 2006/0020098 | A1* | 1/2006 | Miyazawa et al. ............ 528/28 |
| 2007/0141104 | A1 | 6/2007 | Hauenstein |
| 2008/0113942 | A1 | 5/2008 | Suda et al. |
| 2008/0300375 | A1 | 12/2008 | Suda et al. |

FOREIGN PATENT DOCUMENTS

| | | |
|---|---|---|
| JP | 56-135492 | 10/1981 |
| JP | 60-067489 | 4/1985 |
| JP | 06-510322 | 11/1994 |

(Continued)

OTHER PUBLICATIONS

Extended European search report mailed Apr. 18, 2011.

(Continued)

*Primary Examiner* — William Cheung
(74) *Attorney, Agent, or Firm* — IPUSA, PLLC

(57) ABSTRACT

A polysiloxane includes a structural unit in which a functional group represented by a general formula of

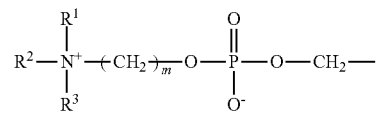

(in the formula, each of $R^1$, $R^2$, and $R^3$ is independently an alkyl group with a carbon number of 1 or more and 6 or less and m is an integer of 2 or more and 6 or less), an ester bond or an amide bond, a spacer, and a silicon atom are bonded sequentially.

5 Claims, 10 Drawing Sheets

FOREIGN PATENT DOCUMENTS

| | | |
|---|---|---|
| JP | 07-118123 | 5/1995 |
| JP | 09-003132 | 1/1997 |
| JP | 10-298340 | 11/1998 |
| JP | 2000-279512 | 10/2000 |
| JP | 2002-098676 | 4/2002 |
| JP | 2003-040942 | 2/2003 |
| JP | 2004-175830 | 6/2004 |
| JP | 2006-008661 | 1/2006 |
| JP | 2006-008987 | 1/2006 |
| JP | 2006-011380 | 1/2006 |
| JP | 2006-199749 A | 8/2006 |
| JP | 2007-119643 | 5/2007 |
| JP | 2007-169163 | 7/2007 |

OTHER PUBLICATIONS

Goda T el al: "Biomimetic phosphorylcholine polymer grafting from polydimethylsiloxane surface using photo-induced polymerization", Biomaterials, Elsevier Science Publishers BV., Barking, GB, vol. 27, No. 30, Oct. 1, 2006, pp. 5151-5160, XP025097409.

Iwasaki et al: "Surface modification with well-defined biocompatible triblock copolymers", Colloids and Surfaces. B, Biointerfaces, Elsevier, Amsterdam, NL, vol. 57, No. 2, May 1, 2007, pp. 226-236, XP022053583.

Seo et al: "Surface tethering of phosphorylcholine groups onto poly(dimethylsiloxane) through swelling-deswelling methods with phospholipids moiety containing ABA-type block copolymers", Biomaterials, Elsevier Science Publishers BV., Barking, GB. vol. 29, No. 10, Dec. 26, 2007, pp. 1367-1376, XP022433824.

Mitsuaki Yamada et al: "Synthesis of Novel Organopolysiloxanes Having a Phospholipid-Like Structure", Macromolecules, American Chemical Society, US, vol. 28, No. 7, Mar. 27, 1995, XP000494860.

Akio Furukawa et al., Synthesis and polymerization of 10-(11-methacryloyloxy-undecyloxycarbonyl)decyl 2-(trimethylammonio)ethylphosphate, Makromol. Chem., 187, 311-316 (1986).

Eric A. Angu, et al. "Underwater captive bubble technique on curved surfaces of blended polydimethylsiloxanes" Journal of Adhesion Science and Technology, vol. 13 No. 10 pp. 1225-1240 1999.

\* cited by examiner

POLYSILOXANE, ACRYLIC COMPOUND AND VINYLIC COMPOUND

TECHNICAL FIELD

The present invention relates to a polysiloxane, a method of manufacturing a polysiloxane, an acrylic compound, a method of manufacturing an acrylic compound, an acrylic polymer, a vinylic compound, a method of manufacturing a vinylic compound, a surface modifying agent, and a method of modifying a surface.

BACKGROUND ART

Conventionally, a polymer having a phosphorylcholine group is known as a biocompatible polymer and a biocompatible material is known in which each kind of resin material is coated with such a polymer.

Patent document 1 discloses a cosmetic powder in which a powder is coated with a polymer obtainable by polymerizing 2-methacryloyloxyethylphosphorylcholine as one monomer.

Furthermore, patent document 2 discloses a medical material in which a coating layer composed of heparin or a heparin derivative and a copolymer based on a monomer having a phosphorylcholine-like group on a side chain and a monomer having a group capable of bonding to heparin or a heparin derivative is formed on a surface of a substrate.

Moreover, patent document 3 discloses a separation material having a phosphorylcholine-like group on at least a surface thereof, wherein the ratio (P/C) of the amount of a phosphorus element originating from a phosphorylcholine-like group to the amount of a carbon element is 0.002-0.3 in a spectrum measured by an X-ray photoelectron spectroscopic analysis with respect to the surface.

Meanwhile, patent document 4 discloses a polysiloxane having a phosphorylcholine group. However, in such a polysiloxane, a phosphorylcholine group is bonded to a silicon atom via an imino group having a pH dependency, whereby a problem is that a pH for obtaining an effect of a phosphorylcholine group is limited when used as a surface modifying agent.

Furthermore, patent document 5 discloses a copolymer of 2-methacryloyloxyethylphosphorylcholine (MPG) and a methacrylic acid ester. Moreover, patent document 6 discloses a method for manufacturing a polymer containing a phosphorylcholine group.

Additionally, for example, 2-chloro-1,3,2-dioxaphosphorane-2-oxide is reacted with 2-hydroxyethyl methacrylate and subsequently reacted with trimethylamine, whereby it may be possible to obtain MPG. However, in regard to thus obtained acrylic compound having a phosphorylcholine-like group, a synthetic method thereof is complicated and a hydrolysis resistance thereof is insufficient.

Patent document 1: Japanese Patent Application Publication No. H07-118123
Patent document 2: Japanese Patent Application Publication No. 2000-279512
Patent document 3: Japanese Patent Application Publication No. 2002-098676
Patent document 4: Japanese Patent Application Publication No. 2004-175830
Patent document 5: Japanese Patent Application Publication No. H09-003132
Patent document 6: Japanese Patent Application Publication No. H10-298240

DISCLOSURE OF THE INVENTION

Problems to be Solved by the Invention

According to one aspect of the present invention, there is provided a polysiloxane including a structural unit having a functional group represented by a general formula of

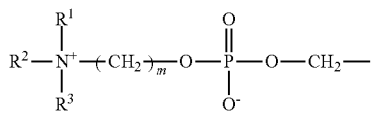

wherein each of $R^1$, $R^2$, and $R^3$ is independently an alkyl group with a carbon number of 1 or more and 6 or less and m is an integer of 2 or more and 6 or less, an ester bond or an amide bond, a spacer, and a silicon atom in sequence.

According to another aspect of the present invention, there is provided a method of manufacturing the polysiloxane as described above, including a step of oxidizing glycerophosphorylcholine to synthesize a compound having a carboxyl group or a phosphorylcholine group.

According to another aspect of the present invention, there is provided a surface modifying agent containing the polysiloxane as described above.

According to another aspect of the present invention, there is provided an acrylic compound containing a functional group represented by a general formula of

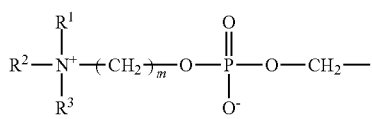

wherein each of $R^1$, $R^2$, and $R^3$ is independently an alkyl group with a carbon number of 1 or more and 6 or less, and m is an integer of 2 or more and 6 or less, an ester bond or an amide bond, a spacer, an ester bond or amide bond, and a functional group represented by a general formula of

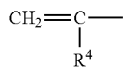

wherein $R^4$ is a hydrogen atom or an alkyl group with a carbon number of 1 or more and 18 or less, in sequence.

According to another aspect of the present invention, there is provided a method of manufacturing the acrylic compound as described above, including a step of oxidizing glycerophosphorylcholine to synthesize a compound having a carboxyl group and a phosphorylcholine group.

According to another aspect of the present invention, there is provided a surface modifying agent containing the acrylic compound as described above.

According to another aspect of the present invention, there is provided an acrylic polymer, wherein the acrylic polymer is a homopolymer or copolymer of the acrylic compound as described above.

According to another aspect of the present invention, there is provided a surface modifying agent containing the acrylic polymer as described above.

According to another aspect of the present invention, there is provided a vinylic compound containing a functional group represented by a general formula of

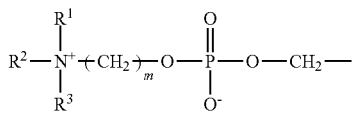

wherein each of $R^1$, $R^2$, and $R^3$ is independently an alkyl group with a carbon number of 1 or more and 6 or less and m is an integer of 2 or more and 6 or less, an ester bond or an amide bond, a spacer, and a functional group represented by a general formula of

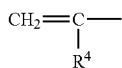

wherein $R^4$ is a hydrogen atom or an alkyl group with a carbon number of 1 or more and 18 or less, in sequence.

According to another aspect of the present invention, there is provided a method of manufacturing the vinylic compound as described above, including a step of oxidizing glycerophosphorylcholine to synthesize a compound having a carboxyl group and a phosphorylcholine group.

According to another aspect of the present invention, there is provided a surface modifying agent containing the vinylic compound as described above.

According to another aspect of the present invention, there is provided a method of modifying a surface, including a step of using the surface modifying agent as described above to modify a material surface.

BEST MODE FOR CARRYING OUT THE INVENTION

Figure 1:
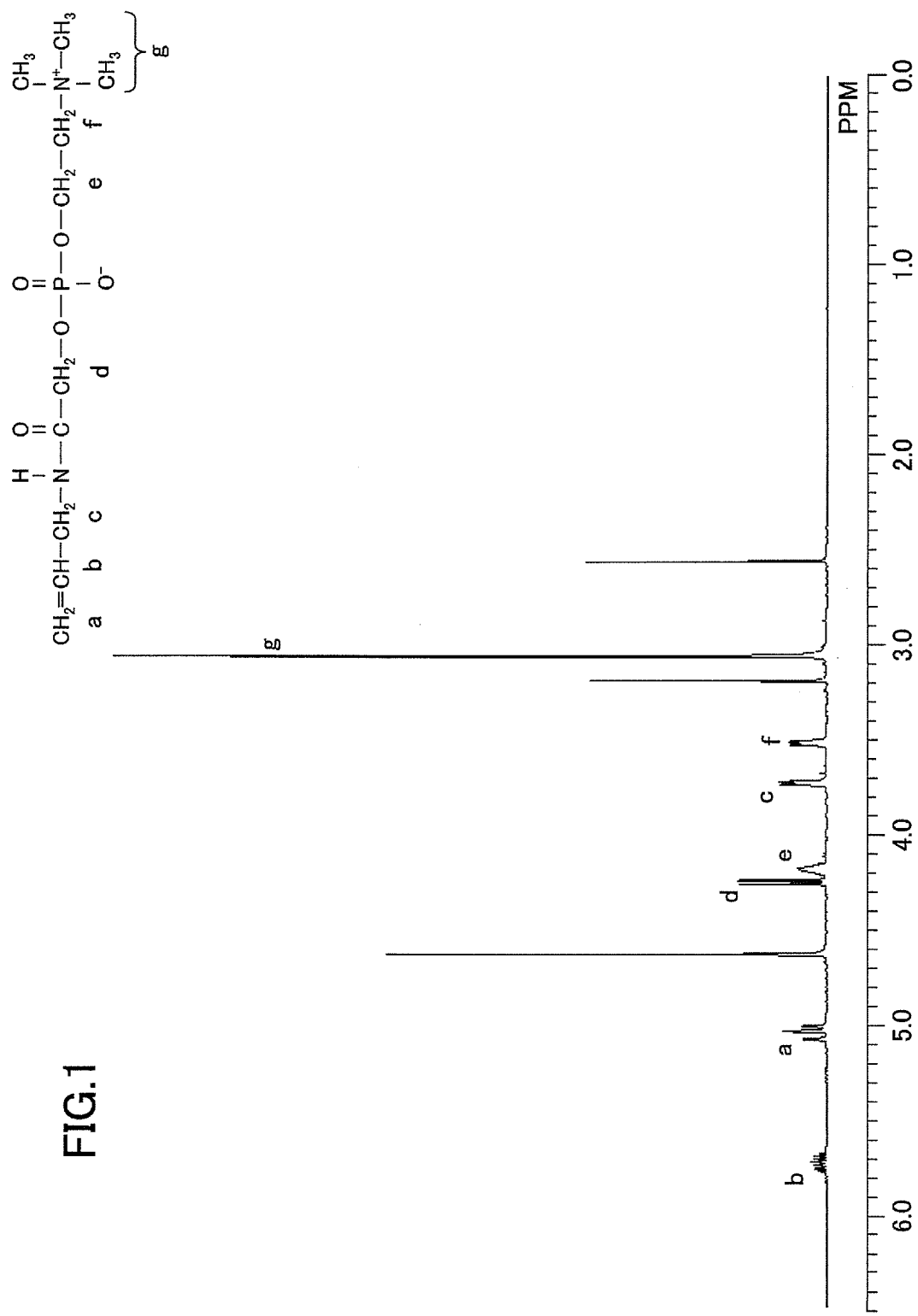
FIG. 1 is a diagram illustrating an $^1$H NMR spectrum of compound B in practical example 1.

Next, the best mode for carrying out the present invention will be described in conjunction with the drawings.

[Polysiloxane]

A polysiloxane according to the present invention has a structural unit in which a group represented by a general formula of

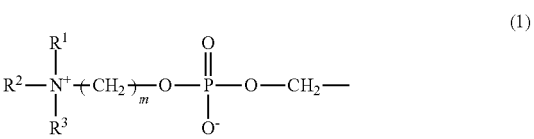

(in the formula, each of $R^1$, $R^2$, and $R^3$ is independently an alkyl group with a carbon number of 1-6 and m is an integer of 2-6), an ester bond or an amide bond, a spacer, and an Si atom are bonded sequentially. Thereby, it may be possible to obtain a polysiloxane having a phosphorylcholine-like group and being capable of controlling a limitation to a pH. Additionally, it may be possible for such a polysiloxane, whether purified or unpurified, to modify a material surface, whereby it may be possible to obtain an effect of controlling adsorption of a protein or the like.

A polysiloxane according to the present invention preferably has a structural unit represented by a general formula of

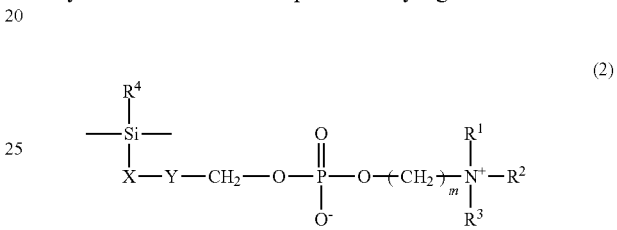

(in the formula, $R^4$ is a hydrogen atom or an alkyl group with a carbon number of 1-18, X is an alkylene group with a carbon number of 1-18, a polyoxyalkylene group with a unit number of 1-18, or an arylene group, and Y is an ester bond or amide bond). Herein, for a polyoxyalkylene group, there is provided a polyoxyethylene group, a polyoxypropylene group, or the like. For an arylene group, there is provided a phenylene group, an oxyphenylene group, a methylenephenylene group, or the like. In addition, any of an alkylene group, polyoxyalkylene group, and arylene group may be substituted with another hydrocarbon-type functional group.

The ratio of a structural unit represented by general formula (2) to all of structural units of a polysiloxane according to the present invention is preferably 5% by mole or more, and more preferably 20% by mole or more. Thereby, it may be possible to sufficiently develop a characteristic of such a phosphorylcholine-like group such as biocompatibility or moisture retention thereof.

A polysiloxane according to the present invention may be obtained by condensing a compound having a phosphorylcholine-like group represented by general formula (1) and a carboxyl group with a polysiloxane having a structural unit in which a hydroxyl group or an amino group and an Si atom are bonded via a spacer.

Alternatively, a polysiloxane according to the present invention may be obtained by condensing a compound having a phosphorylcholine-like group represented by general formula (1) and a hydroxyl group or an amino group with a polysiloxane having a structural unit in which a carboxyl group and an Si atom are bonded via a spacer.

Herein, for example, glycerophosphorylcholine may be oxidized by using periodic acid and ruthenium trichloride to obtain a compound having a phosphorylcholine group and a carboxyl group. Furthermore, a compound having a phosphorylcholine group and a carboxyl group may be condensed with a diol or a diamine to obtain a compound having a phosphorylcholine group and a hydroxyl group or an amino group.

Alternatively, a polysiloxane according to the present invention may be obtained by adding (hydrosilylating) a vinylic compound in which a phosphorylcholine-like group represented by general formula (1), an ester bond or an amide bond, a spacer, and a group represented by general formula of

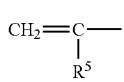

(3)

(in the formula, $R^5$ is a hydrogen atom or an alkyl group with a carbon number of 1-18) are bonded sequentially, to a polysiloxane having a structural unit represented by a general formula of

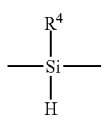

(4)

For a vinylic compound, it is preferable to provide a compound represented by a general formula of

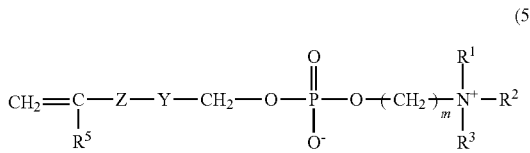

(5)

(in the formula, Z is a group such that a group represented by a general formula of

—CH$_2$CHR$^5$—Z— or a group represented by a general formula of

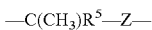

—C(CH$_3$)R$^5$—Z— is X).

A vinylic compound may be obtained by condensing a compound having a phosphorylcholine-like group represented by general formula (1) and a carboxyl group with a compound in which a functional group represented by general formula (3) and a hydroxyl group or an amino group are bonded via a spacer.

Alternatively, a vinylic compound may be obtained by condensing a compound having a phosphorylcholine-like group represented by general formula (1) and a hydroxyl group or an amino group with a compound in which a functional group represented by general formula (3) and a carboxyl group are bonded via a spacer.

Herein, for example, glycerophosphorylcholine may be oxidized by using periodic acid and ruthenium trichloride to obtain a compound having a phophorylcholine group and a carboxyl group. Furthermore, a compound having a phosphorylcholine group and a carboxyl group may be condensed with a diol or a diamine to obtain a compound having a phosphorylcholine group and a hydroxyl group or an amino group.

A polysiloxane according to the present invention may be used as a surface modifying agent, wherein a material surface may be modified by introducing a desired quantity of a phosphorylcholine-like group thereinto. Herein, for a material with a surface capable of being modified, there is provided a polyethylene, a polypropylene, a polystyrene, a polyvinyl chloride, a nylon, a polyurethane, a polyurea, a poly(meth) acrylic acid, a poly(meth)acrylate, a polyester, a polyacrylonitrile, a polyacrylamide, a polyvinyl acetate, a polycarbonate, a polysulfone, a polyvinyl alcohol, a cellulose, a cellulose acetate, a silicone resin, a glass, a ceramic, a metal, a stainless steel, or the like, and two kinds or more thereof may be used in combination.

When a polysiloxane according to the present invention is used to modify a material surface, a solution or dispersion fluid of a polysiloxane is preferably applied onto and dried on a material surface. Herein, drying under a reduced pressure, heating treatment, or the like may be conducted according to need. A solvent to be used for a solution or dispersion fluid of a polysiloxane is not particularly limited. The concentration of a polysiloxane in a solution or dispersion fluid is preferably 0.01-30% by weight, and more preferably 0.1-20% by weight. If this concentration is less than 0.01% by weight, the amount of a polysiloxane to be formed on a material surface may be insufficient so that a performance thereof may not be developed. On the other hand, if the concentration is more than 30% by weight, workability for applying a solution or dispersion fluid of a polysiloxane may be deteriorated so that the uniformity of a coating film may be degraded. Additionally, for an application method, there is provided, for example, a publicly known method such as a dipping method, a spray method, a roller coating method, or a spin-coating method.

[Acrylic Compound]

In an acrylic compound according to the present invention, a phosphorylcholine-like group represented by a general formula of

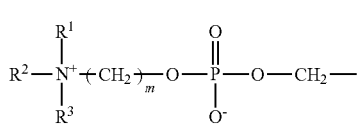

(1)

(in the formula, each of $R^1$, $R^2$, and $R^3$ is independently an alkyl group with a carbon number of 1-6 and m is an integer of 2-6), an ester bond or an amide bond, a spacer, an ester bond or an amide bond, and a functional group represented by a general formula of

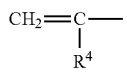

(6)

(in the formula, $R^4$ is a hydrogen atom or an alkyl group with a carbon number of 1-18) are bonded sequentially. Thereby, it may be possible to obtain an acrylic compound excellent in a hydrolysis resistance thereof. Additionally, it may be possible for such an acrylic compound, whether purified or unpurified, to modify a material surface, whereby it may be possible to obtain an effect of controlling adsorption of a protein or the like.

Furthermore, an acrylic compound according to the present invention is preferably a compound represented by a general formula of

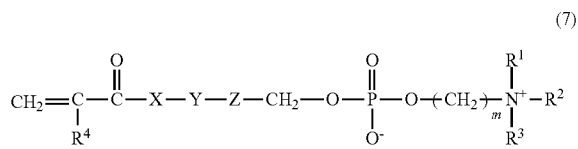
(7)

(in the formula, X is an oxy group or an imino group, Y is an alkylene group with a carbon number of 1-18, a polyoxyalkylene group with a unit number of 1-18, or an arylene group, and Z is an ester bond or an amide bond). Herein, for a polyoxyalkylene group, there is provided a polyoxyethylene group, a polyoxypropylene group, or the like. For an arylene group, there is provided a phenylene group, a hydroxyphenylene group, a phenylenemethylene group, or the like. In addition, any of an alkylene group, polyoxyalkylene group and arylene group may be substituted with another hydrocarbon-type functional group.

An acrylic compound according to the present invention may be obtained by condensing a compound having a phosphorylcholine-like group represented by general formula (1) and a carboxyl group with a compound in which a functional group represented by general formula (6), an ester bond or an amide bond, a spacer, and a hydroxyl group or an amino group are bonded sequentially.

Alternatively, an acrylic compound according to the present invention may be obtained by condensing a compound having a phosphorylcholine-like group represented by general formula (1) and a hydroxyl group or an amino group with a compound in which a functional group represented by general formula (6), an ester bond or an amide bond, a spacer, and a carboxyl group are bonded sequentially.

Herein, for example, glycerophosphorylcholine may be oxidized by using periodic acid and ruthenium trichloride to obtain a compound having a phosphorylcholine group and a carboxyl group. Furthermore, a compound having a phosphorylcholine group and a carboxyl group may be condensed with a diol or a diamine, whereby it may be possible to obtain a compound having a phosphorylcholine group and a hydroxyl group or an amino group.

An acrylic compound may be used as a surface modifying agent, wherein a material surface may be modified by introducing a desired quantity of a phosphroyloholine-like group thereinto. Herein, for a material with a surface capable of being modified, there is provided a polyethylene, a polypropylene, a polystyrene, a polyvinyl chloride, a nylon, a polyurethane, a polyurea, a poly(meth)acrylic acid, a poly(meth)acrylate, a polyester, a polyacrylonitrile, a polyacrylamide, a polyvinyl acetate, a polycarbonate, a polysulfone, a polyvinyl alcohol, a cellulose, a cellulose acetate, a silicone resin, a glass, a ceramic, a metal, a stainless steel, or the like, and two or more kinds thereof may be used in combination.

When a material surface is modified by using an acrylic compound according to the present invention, it is preferable to treat a material surface by plasma treatment, ozone treatment, or the like, and subsequently apply a solution or dispersion fluid of an acrylic compound onto the material surface, whereby the acrylic compound is polymerized and grafted. Herein, drying under a reduced pressure, heating treatment, or the like may be conducted according to need. A solvent to be used for a solution or dispersion fluid of an acrylic compound is not particularly limited. The concentration of an acrylic compound in a solution or dispersion fluid is preferably 0.01-30% by weight, and more preferably 0.1-20% by weight. If this concentration is less than 0.01% by weight, the amount of an acrylic compound to be formed on a material surface may be insufficient so that a performance thereof may not be developed. On the other hand, if the concentration is more than 30% by weight, workability for applying a solution or dispersion fluid of an acrylic compound may be deteriorated so that the uniformity of a coating film may be degraded. Additionally, for an application method, there is provided, for example, a publicly-known method such as a dipping method, a spray method, a roller coating method, or a spin-coating method.

[Acrylic Polymer]

An acrylic polymer according to the present invention may be obtained by radical-polymerizing an acrylic compound according to the present invention in a solvent under the presence of a polymerization initiator. A solvent is not particularly limited as long as a monomer is soluble therein, and there is provided water, methanol, ethanol, propanol, t-butanol, benzene, toluene, dimethylfoxmamide, tetrahydrofuran, chloroform, or the like, wherein two or more kinds thereof may be used in combination.

Furthermore, a polymerization initiator is not particularly limited, and there is provided, for example, an organic peroxide such as benzoyl peroxide, t-butyl peroxy-2-ethylhexanoate, succinyl peroxide, glutar peroxide, succinyl peroxyglutarate, t-butyl peroxymalate, t-butyl peroxypivalate, di-2-ethoxyethyl peroxycarbonate, or 3-hydroxy-1,1-dimethylbutyl peroxypivalate, an azo compound such as azobisisobutyronitrile, dimethyl 2,2-azobis(isobutyrate), 1-((1-cyano-1-methylethyl)azo)formamide, 2,2-azobis(2-methyl-N-phenylpropionamidine)dihydrochloride, 2,2-azobis(2-methyl-N-(2-hydroxyethyl)propionamide), 2,2-azobis(2-methylpropionamide)dihydrate, 4,4-azobis(4-cyanopentanoic acid), 2,2-azobis(2-(hydroxymethyl)propionitrile), or the like, wherein two or more kinds thereof may be used in combination. Preferably, 0.001-10% by weight, and more preferably 0.01-5% by weight, of a polymerization initiator is added into a monomer solution.

Additionally, an acrylic compound according to the present invention may be copolymerized with another monomer. Another monomer is not particularly limited and a monofunctional monomer is preferable, wherein there is provided, for example, (meth)acrylic acid; a (meth)acrylate such as methyl(meth)acrylate, ethyl(meth)acrylate, propyl(meth)acrylate, butyl(meth)acrylate, hexyl(meth)acrylate, lauryl (meth)acrylate, or stearyl(meth)acrylate; a hydroxyalkyl (meth)acrylate such as 2-hydroxyethyl(meth)acrylate or 2-hydroxypropyl(meth)acrylate; (meth)acrylamide; a styrene-type monomer such as styrene, methylstyrene, or a substituted styrene; a vinyl ether such as ethyl vinyl ether or butyl vinyl ether; N-vinylpyrolidone; an unsaturated hydrocarbon-type monomer or substituted unsaturated hydrocarbon-type monomer such as vinyl chloride, vinylidene chloride, ethylene, propylene, or isobutylene; acrylonitrile; glyco-2-hydroxyethyl monomethacrylate (GEMA); oligo(ethylene glycol)monomethacrylate; polyethylene glycol monomethacrylate; or the like, and two or more kinds thereof may be used in combination.

Herein, the ratio of an acrylic compound according to the present invention to the total amount of a monomer(s) is preferably 5% by mole or more, and more preferably 20% by mole or more. Thereby, it may be possible to sufficiently develop a characteristic of a phosphorylcholine-like group such as biocompatibility or moisture retention thereof.

Furthermore, the concentration of a monomer in a solution is preferably 0.01-2 mol/l. When the concentration of a monomer is equal to or more than 0.01 mol/l, it may be possible to improve the efficiency of an initiator, and when the concentration is equal to or less than 2 mol/l, it may be possible to reduce abnormal polymerization or gelation.

A polymerization temperature is usually 5-100° C. When a polymerization temperature is equal to or higher than 5° C., it may be possible to accelerate a polymerization reaction, and when equal to or lower than 100° C., it may be possible to reduce decomposition of a phosphorylcholine-like group which is caused by a high temperature. A period of time for polymerization is usually 10 minutes-24 hours, and preferably 30 minutes-12 hours.

An acrylic polymer according to the present invention may be used as a surface modifying agent, wherein a material surface may be modified by introducing a desired quantity of a phosphorylcholine-like group thereinto. Herein, for a material with a surface capable of being modified, there is provided a polyethylene, a polypropylene, a polystyrene, a polyvinyl chloride, a nylon, a polyurethane, a polyurea, a poly(meth)acrylic acid, a poly(meth)acrylate, a polyester, a polyacrylonitrile, a polyacrylamide, a polyvinyl acetate, a polycarbonate, a polysulfone, a polyvinyl alcohol, a cellulose, a cellulose acetate, a silicone resin, a glass, a ceramic, a metal, a stainless steel, or the like, and two or more kinds thereof may be used in combination.

When an acrylic polymer according to the present invention is used to modify a material surface, a solution or dispersion fluid of an acrylic polymer is preferably applied onto and dried on a material surface. Herein, drying under a reduced pressure, heating treatment, or the like may be conducted according to need. A solvent to be used for a solution or dispersion fluid of an acrylic polymer is not particularly limited. The concentration of an acrylic polymer in a solution or dispersion fluid is preferably 0.01-30% by weight, and more preferably 0.1-20% by weight. If this concentration is less than 0.01% by weight, the amount of an acrylic polymer to be formed on a material surface may be insufficient so that a performance thereof may not be developed. On the other hand, if the concentration is more than 30% by weight, workability for applying a solution or dispersion fluid of an acrylic polymer may be deteriorated so that the uniformity of a coating film may be degraded. Additionally, for an application method, there is provided, for example, a publicly-known method such as a dipping method, a spray method, a roller coating method, or a spin-coating method.

[Vinylic Compound]

In a vinylic compound according to the present invention, a phosphorylcholine-like group represented by a general formula of

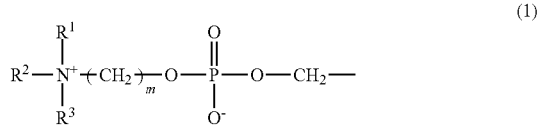

(1)

(in the formula, each of $R^1$, $R^2$, and $R^3$ is independently an alkyl group with a carbon number of 1-6 and m is an integer of 2-6), an ester bond or an amide bond, a spacer, and a functional group represented by a general formula of

(6)

(in the formula, $R^4$ is a hydrogen atom or an alkyl group with a carbon number of 1-18) are bonded sequentially. Thereby, it may be possible to obtain a vinylic compound excellent in a hydrolysis resistance thereof.

Additionally, it may be possible for such a vinyl compound, whether purified or unpurified, to modify a material surface, whereby it may be possible to obtain an effect of controlling adsorption of a protein or the like.

Furthermore, a vinylic compound according to the present invention is preferably a compound represented by a general formula of

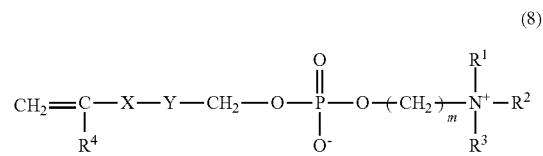

(8)

(in the formula, X is an alkylene group with a carbon number of 1-18, a polyoxyalkylene group with a unit number of 1-18, or an arylene group, and Y is an ester bond or an amide bond). Herein, for a polyoxyalkylene group, there is provided a polyoxyethylene group, a polyoxypropylene group, or the like. For an arylene group, there is provided a phenylene group, an oxyphenylene group, a methylenephenylene group, or the like. In addition, any of an alkylene group, polyoxyalkylene group, and arylene group may be substituted with another hydrocarbon functional group.

A vinylic compound according to the present invention may be obtained by condensing a compound having a phosphorylcholine-like group represented by general formula (1) and a carboxyl group with a compound in which a functional group represented by general formula (6) and a hydroxyl group or an amino group are bonded via a spacer.

Alternatively, a vinylic compound according to the present invention may be obtained by condensing a compound having a phosphorylcholine-like group represented by general formula (1) and a hydroxyl group or an amino group with a compound in which a functional group represented by general formula (6) and a carboxyl group are bonded via a spacer.

Herein, for example, glycerophosphorylcholine may be oxidized by using periodic acid and ruthenium trichloride to obtain a compound having a phosphorylcholine group and a carboxyl group. Furthermore, a compound having a phosphorylcholine group and a carboxyl group may be condensed with a diol or a diamine to obtain a compound having a phosphorylcholine group and a hydroxyl group or an amino group.

A vinylic compound according to the present invention may be used as a surface modifying agent, wherein a material surface may be modified by introducing a desired amount of a phosphorylcholine-like group thereinto. Herein, for a material with a surface capable of being modified, there is provided a polyethylene, a polypropylene, a polystyrene, a polyvinyl chloride, a nylon, a polyurethane, a polyurea, a poly(meth)acrylic acid, a poly(meth)acrylate, a polyester, a polyacrylonitrile, a polyacrylamide, a polyvinyl acetate, a polycarbonate, a polysulfone, a polyvinyl alcohol, a cellulose, a cellulose acetate, a silicone resin, a glass, a ceramic, a metal, a stainless steel, or the like, and two or more kinds thereof may be used in combination.

When a vinylic compound according to the present invention is used to modify a material surface, it is preferable to treat a material surface by plasma treatment, ozone treatment, or the like, and subsequently apply a solution or dispersion fluid of a vinylic compound onto a material surface, whereby the vinylic compound is polymerized and grafted. Herein, drying under a reduced pressure, heating treatment, or the like may be conducted according to need. A solvent to be used for a solution or dispersion fluid of a vinylic compound is not particularly limited. The concentration of a vinylic compound in a solution or dispersion fluid is preferably 0.01-30% by weight, and more preferably 0.1-20% by weight. If this concentration is less than 0.01% by weight, the amount of a vinylic compound to be formed on a material surface may be insufficient so that a performance thereof may not be developed. On the other hand, if the concentration is more than 30% by weight, workability for applying a solution or dispersion fluid of a vinylic compound may be deteriorated so that the uniformity of a coating film may be degraded. Additionally, for an application method, there is provided, for example, a publicly-known method such as a dipping method, a spray method, a roller coating method, or a spin-coating method.

Practical Examples

Practical Example 1

An aqueous solution of L-α-glycerophosphorylcholine was cooled in an ice-water bath. Then, after sodium periodate with four times equivalent of L-α-glycerophosphorylcholine was added, a catalyst quantity of ruthenium trichloride was added and agitation was conducted for 3 hours to cause reaction. Then, after methanol was added and agitation was further conducted for 30 minutes, filtration was conducted to eliminate a precipitate. Furthermore, after concentration under a reduced pressure was conducted, drying under a reduced pressure was conducted to obtain compound A represented by a chemical formula of

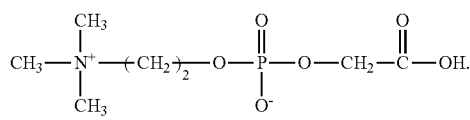

Then, compound A and carbonyldiimidazole (CDI) with two times equivalent of compound A were added into dimethyl sulfoxide (DMSO) and agitation was conducted at room temperature to cause reaction. Furthermore, allylamine was dropped thereinto to cause reaction so that compound B represented by a chemical formula of

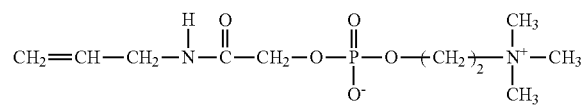

Figure 2:
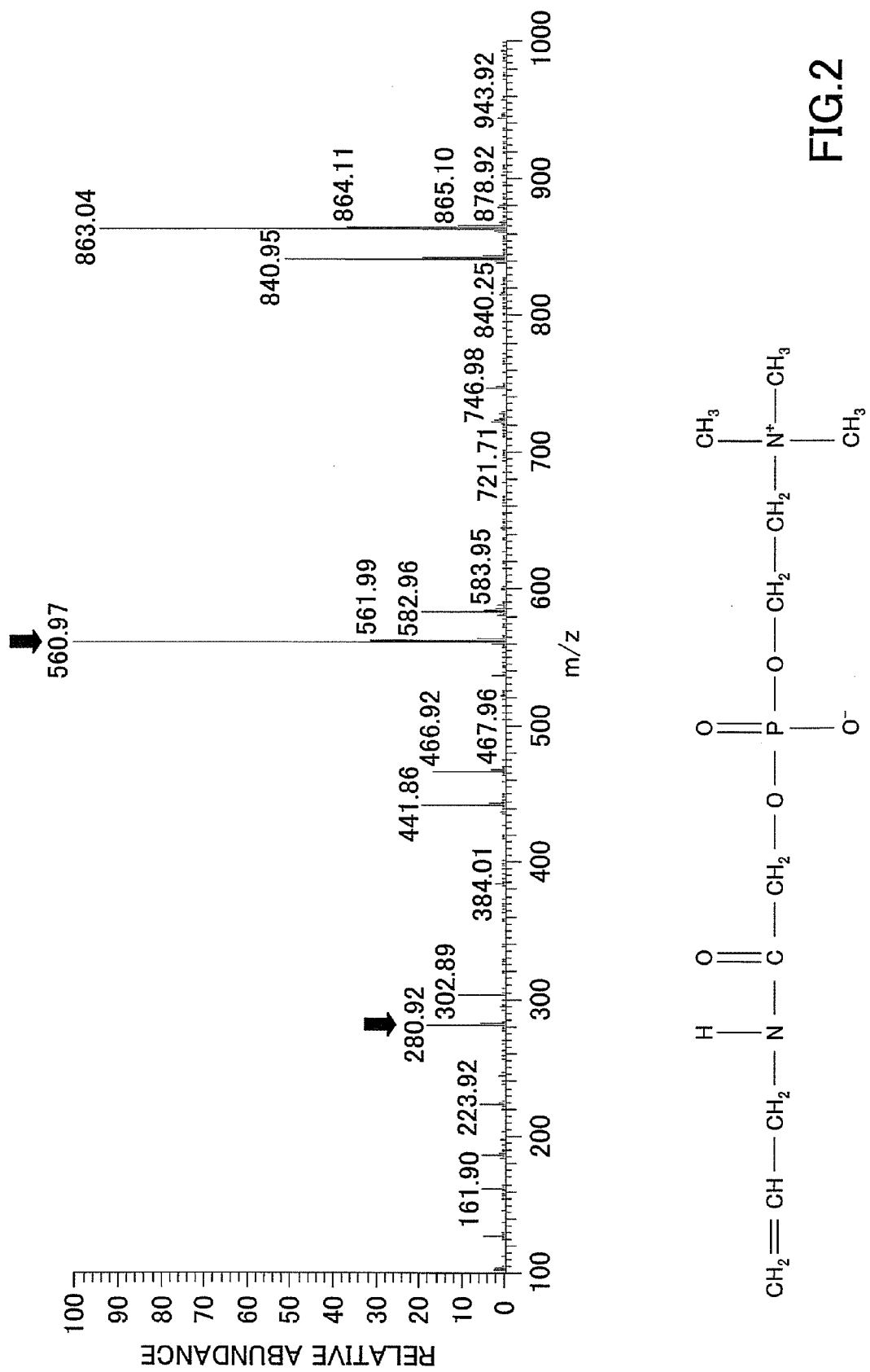
FIG. 2 is a diagram illustrating an MS spectrum of compound B in practical example 1.

(a vinylic compound having a molecular weight of 281 and a phosphorylcholine group) was obtained (see FIG. 1 and FIG. 2).

After a 96-well plate made of polystyrene (produced by Becton, Dickinson and Company Japan) was plasma-treated under argon atmosphere, reaction was conducted with oxygen gas. Then, after dipping in 5% by weight solution of compound B in methanol was conducted and washing with methanol was conducted, drying was conducted to obtain a surface-treated well plate.

[Protein Adsorption Experiment 1]

Proteins were adsorbed to the surface-treated well plate in practical example 1 and an untreated well plate and the amount of an adsorbed protein was quantitatively estimated by using a direct BOA method. The proteins used for such evaluation were three kinds, i.e., albumin (Mw=69000, pI=4.9), γ-globulin (Mw=150000, 5.0<pI<9.5), and lysozyme (Mw=14000, pI=11.0) (all produced by Sigma Corporation).

Figure 3:
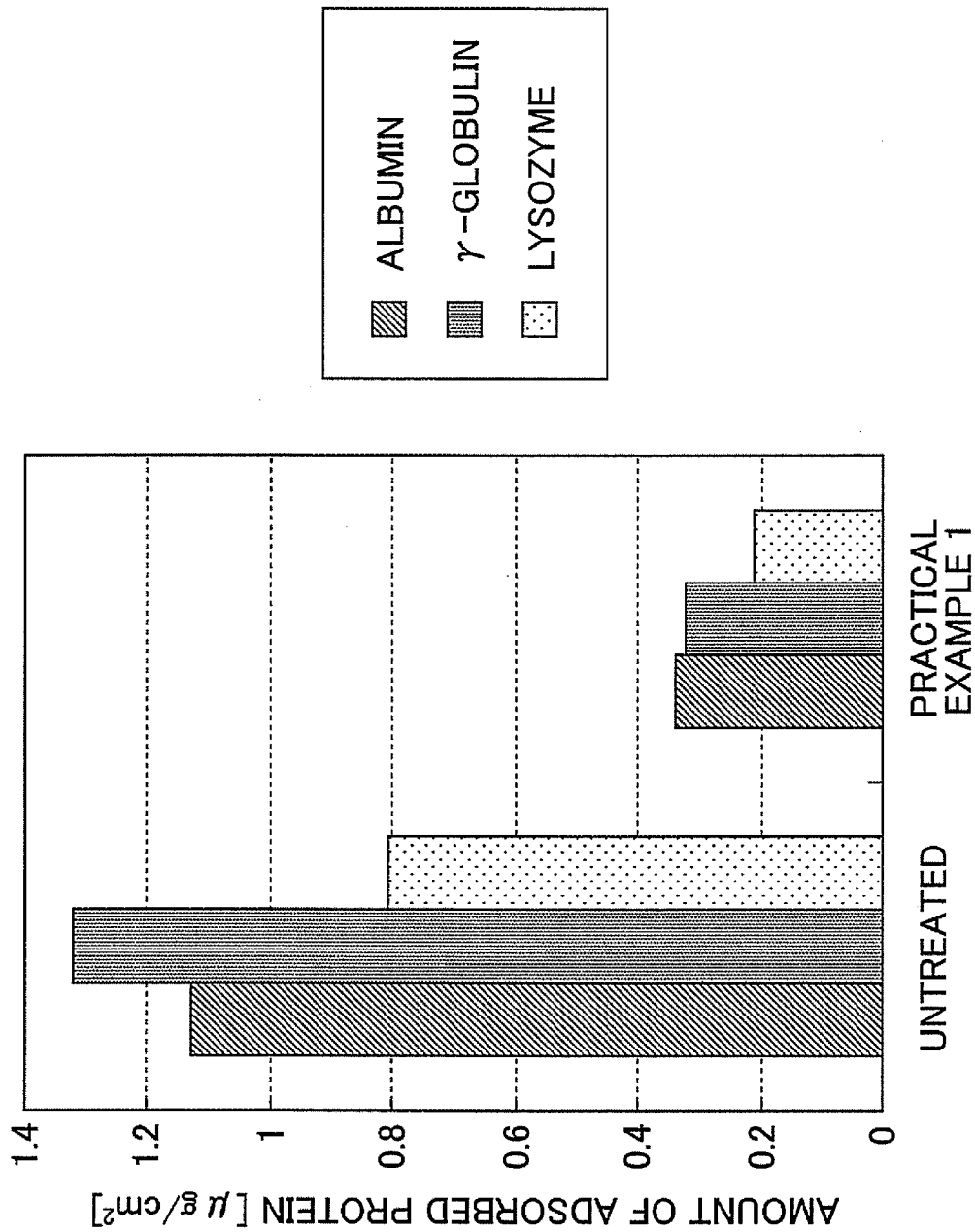
FIG. 3 is a diagram illustrating evaluation results of protein adsorption test 1 in the practical examples.

The method of such an experiment will specifically be described below. First, each protein was dissolved in a phosphate buffer (8 mg/mL of sodium chloride, 0.2 mg/mL of potassium chloride, 1.15 mg/mL of sodium monohydrogen phosphate, and 0.2 mg/mL of potassium dihydrogen phosphate, and pH=7.4) such that the concentration thereof was 0.1 mg/mL, whereby a protein solution was provided. Then, 100 μl of such a protein solution was fed into the wells of the well plates and left at rest at 25° C. for 1 hour. Furthermore, after the wells were washed with 200 μl of the phosphate buffer 5 times, 50 μl of the PBS and 50 μl of a BCA solution were added and leaving at rest was conducted at 60° C. for 1 hour, whereby color development was caused. Then, POWERSCAN HT (produced by Dainippon Sumitomo Pharma Co., Ltd.) as a plate reader was used to measure absorbance with respect to light with a wavelength of 562 nm. Additionally, in order to prepare a calibration curve, absorbance with respect to light with a wavelength of 562 nm was measured similarly to the above, except that after 0, 2, 5, 10, 20, or 40 μl of each protein solution was fed into the wells of the well plates, the PBS was added so as to reach 50 μl and 50 μl of the BCA solution was added. The evaluation results are illustrated in FIG. 3. It is found from FIG. 3 that it may be possible to control adsorption of any protein of albumin, γ-globulin, and lysozyme to a well plate by conducting the surface treatment.

Practical Example 2

Compound B and HM 151 (produced by Gelest Inc.) as a trimethylsiloxy-terminated methyl-H-siloxane-dimethylsiloxane copolymer represented by a chemical formula of

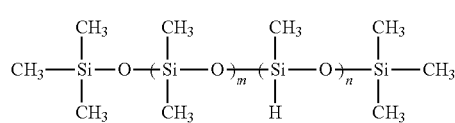

were reacted under the presence of a platinum catalyst $(H_2PtCl_6 \cdot 6H_2O)$ in a mixed liquid of dehydrated ethanol/dehydrated chloroform to obtain compound C represented by a chemical formula of

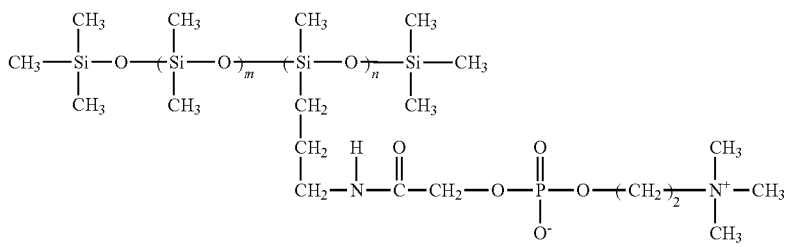

Figure 4:
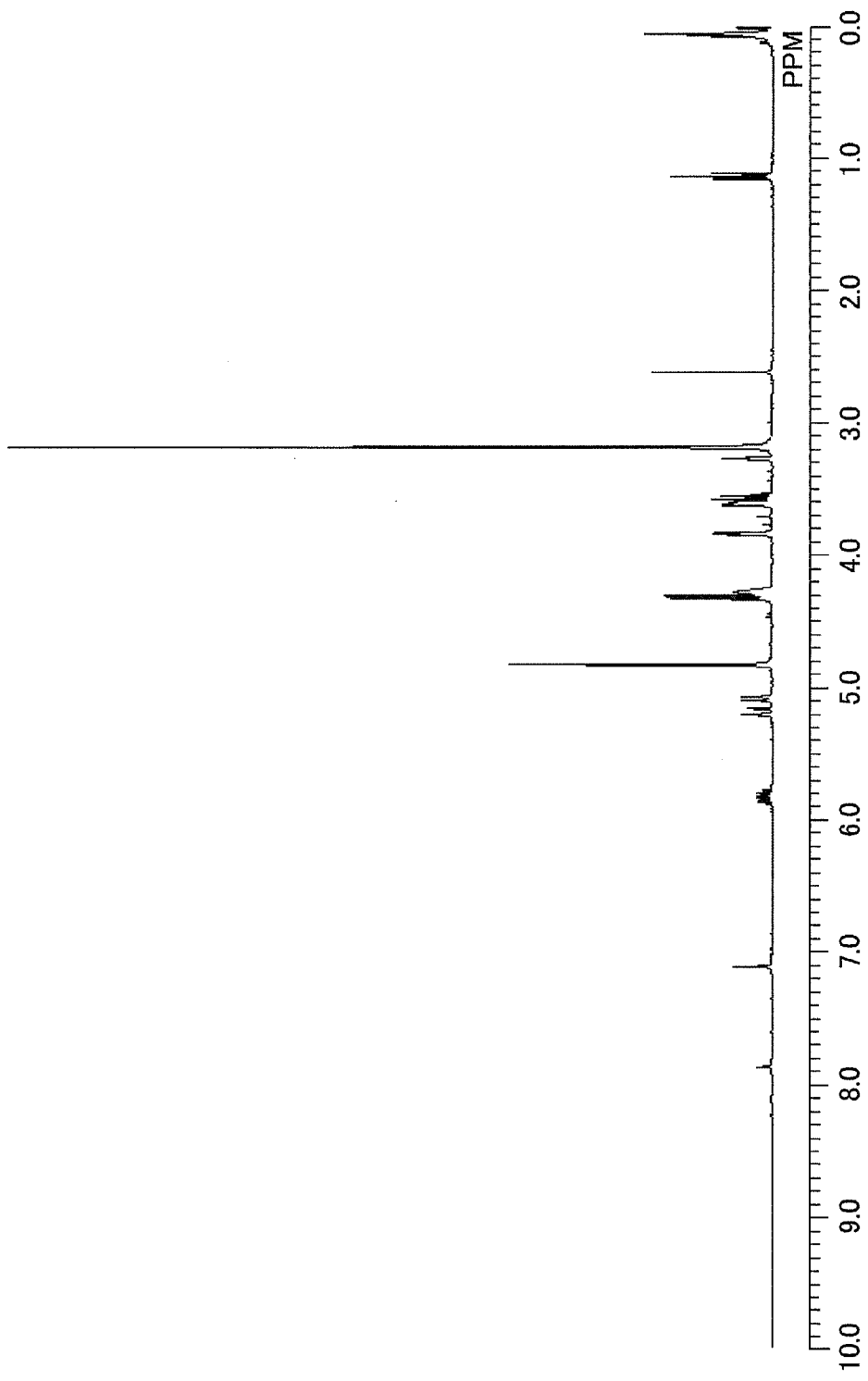
FIG. 4 is a diagram illustrating an $^1$H NMR spectrum of compound C in practical example 2.

(a polysiloxane having a phosphorylcholine group) (see FIG. 4).

10% by weight solution of compound C in methanol was applied to a 96-well plate made of polystyrene (produced by Becton, Dickinson and Company Japan). Then, after washing with methanol was conducted, drying was conducted to obtain a surface-treated well plate.

Practical Example 3

Figure 5:
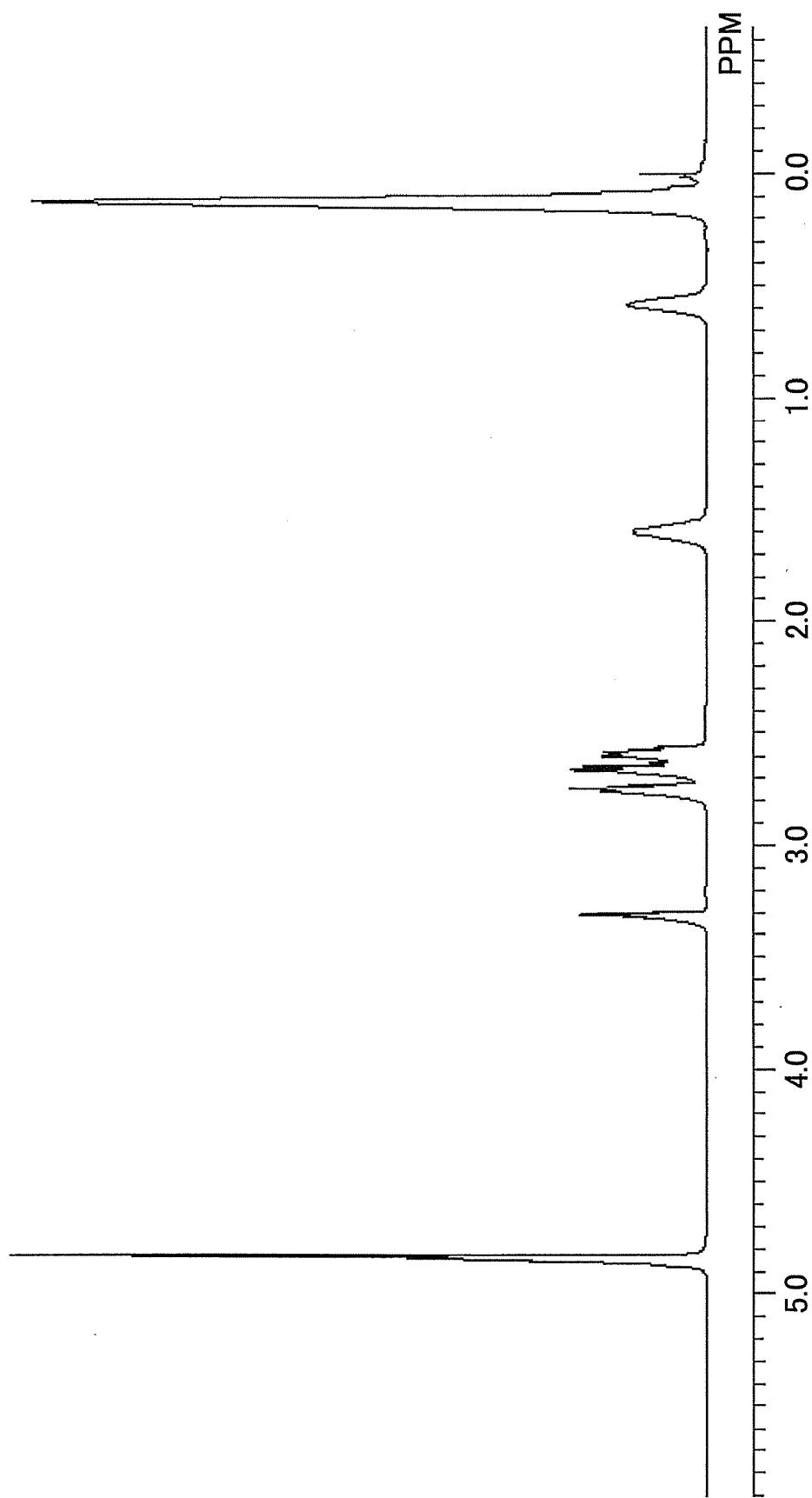
FIG. 5 is a diagram illustrating an $^1$H NMR spectrum of an amino-modified polysiloxane in practical example 3.
Figure 6:
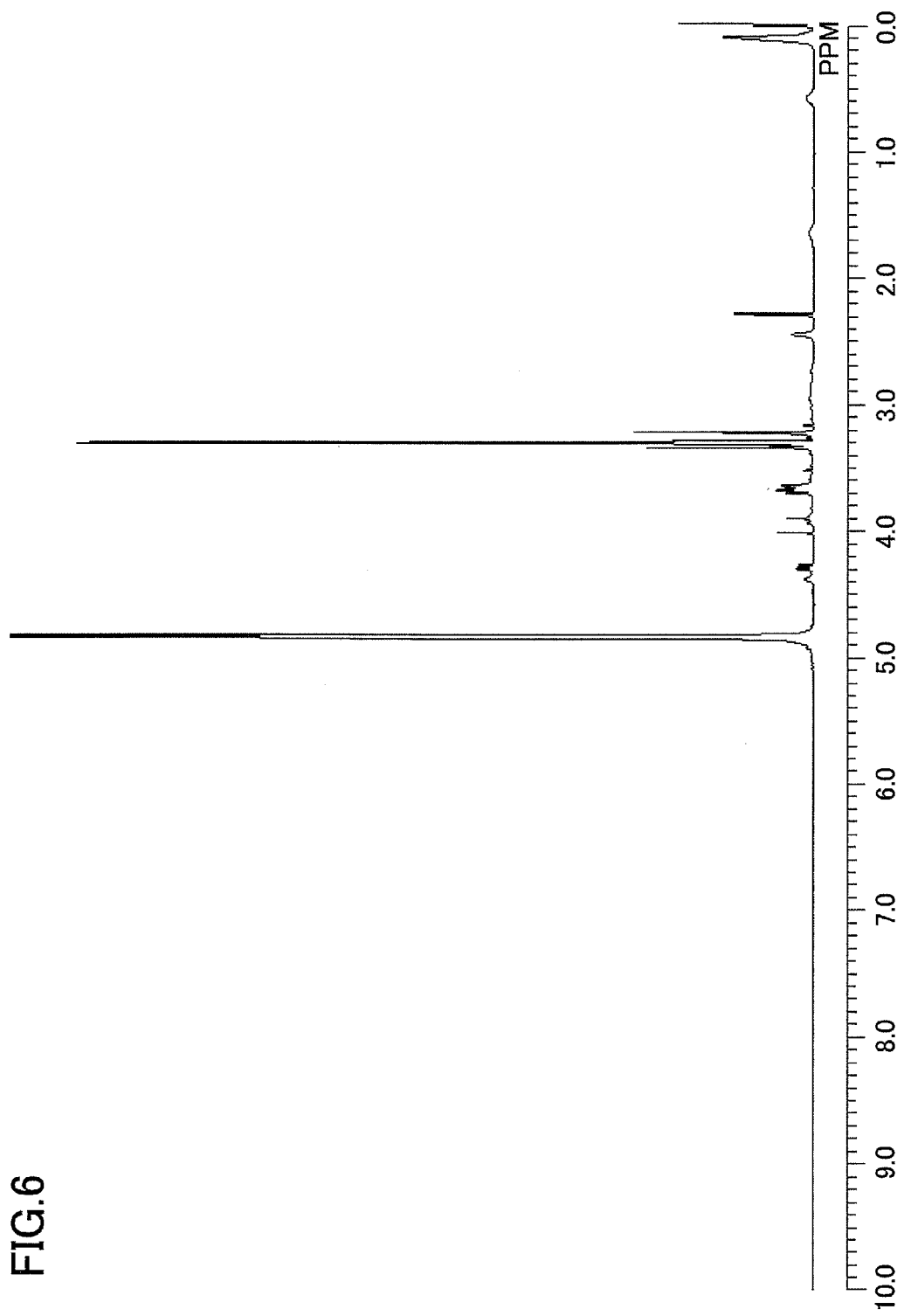
FIG. 6 is a diagram illustrating an $^1$H NMR spectrum of compound D in practical example 3.

After compound A with two times equivalent of a diamine-type amino-modified polysiloxane whose amine equivalent was 144 g/mol (see FIG. 5) was added into a solution of the amino-modified polysiloxane in methanol, a triazine-type dehydration condensation agent DMT-MM (produced by Kokusan Chemical Co., Ltd.) with 1.2 times equivalent of compound A was added and agitation was conducted at room temperature for 3 hours to cause reaction, whereby compound D (a polysiloxane having a phosphorylcholine group) was obtained (see FIG. 6).

10% by weight solution of compound D in methanol was applied to a 96-well plate made of polystyrene (produced by Becton, Dickinson and Company Japan). Then, after washing with methanol was conducted, drying was conducted to obtain a surface-treated well plate.

Comparative Example 1

A surface-treated well plate was obtained similarly to practical example 1 except that 10% by weight solution of a polysiloxane in practical example 2 of patent document 4 in methanol was used.

[Protein Adsorption Experiment 2]

Figure 7:
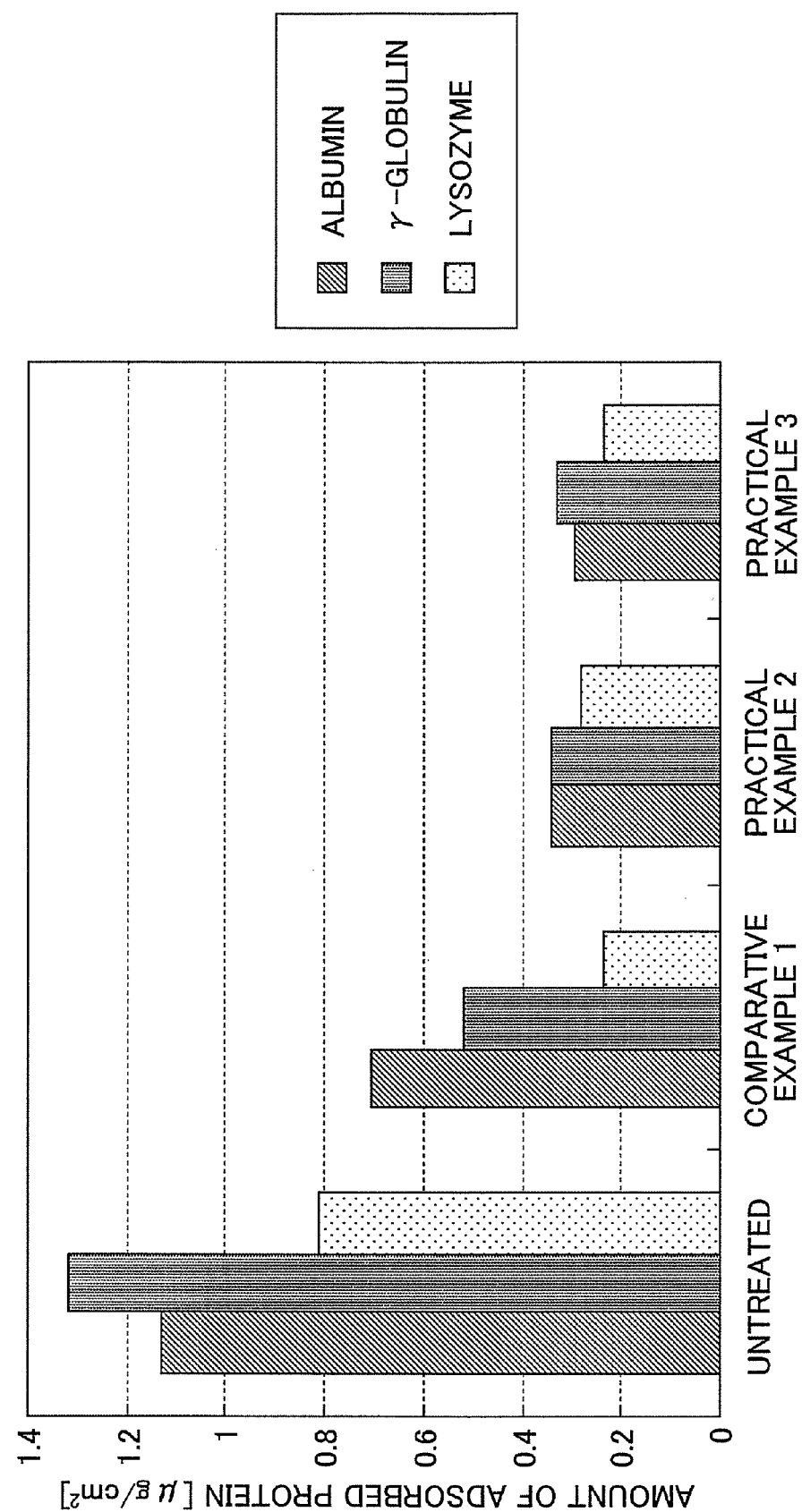
FIG. 7 is a diagram illustrating evaluation results of protein adsorption test 2 in the practical examples.

The amount of an adsorbed protein was quantitatively estimated similarly to protein adsorption experiment 1 except that the surface-treated well plates in practical examples 2 and 3 and comparative example 1 were used instead of the surface-treated well plate in practical example 1. The evaluation results are illustrated in FIG. 7. It is found from FIG. 7 that it may be possible to control adsorption of any protein of albumin, γ-globulin, and lysozyme to a well plate by conducting the surface treatment. Also, it is found that it may be possible for the surface-treated well plates in practical examples 2 and 3 to control adsorption of a protein more non-specifically than the surface-treated well plate in comparative example 1.

Practical Example 4

Compound A and 2-hydroxyethyl methacrylate (HEMA) were added into DMSO and agitation was conducted at room temperature to cause reaction, whereby compound E represented by a chemical formula of

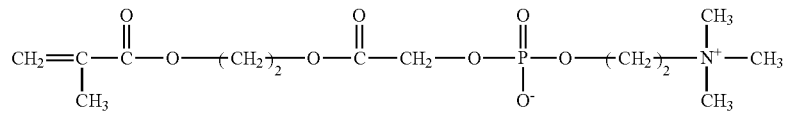

Figure 8:
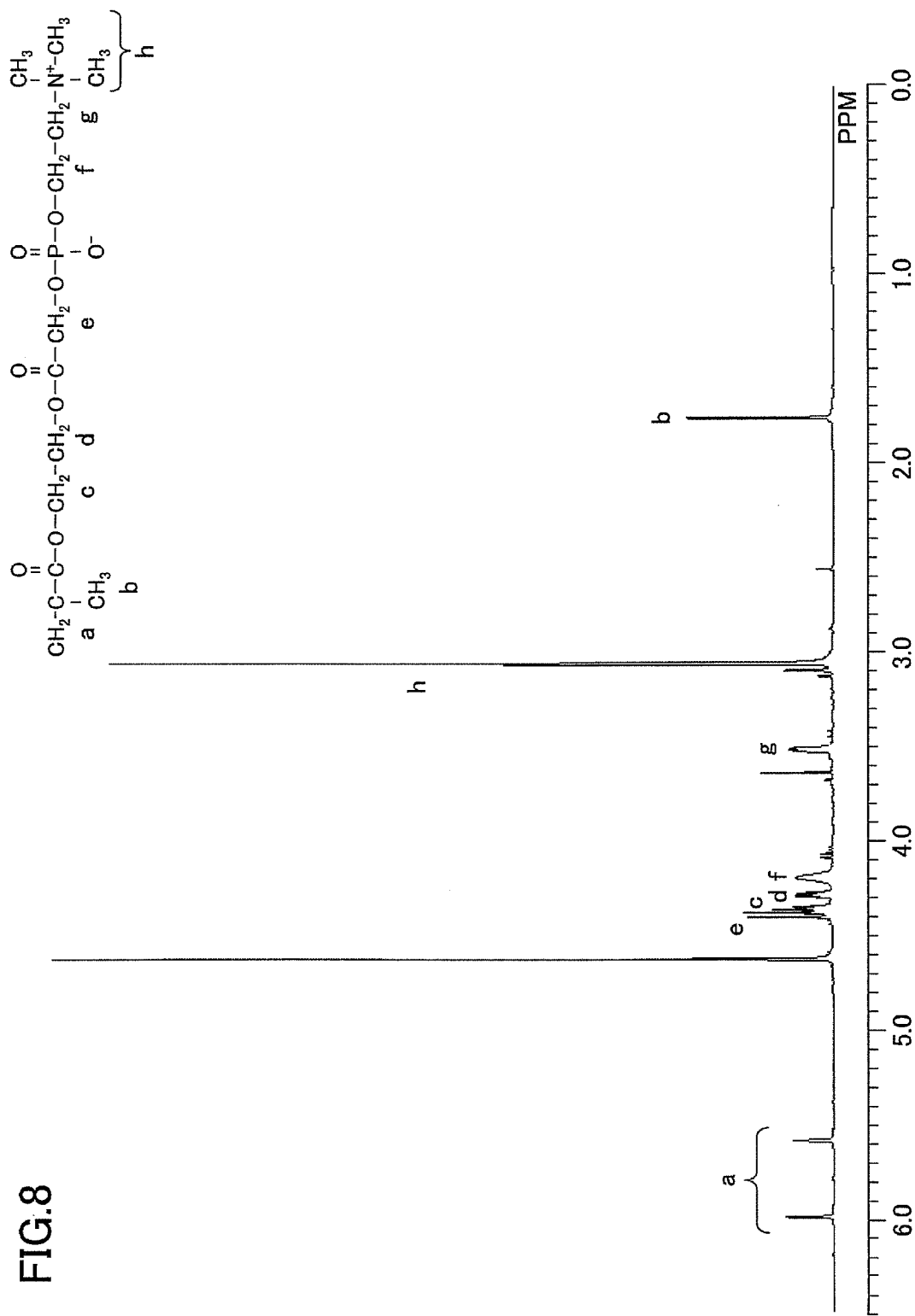
FIG. 8 is a diagram illustrating an $^1$H NMR spectrum of compound E in practical example 4.
Figure 9:
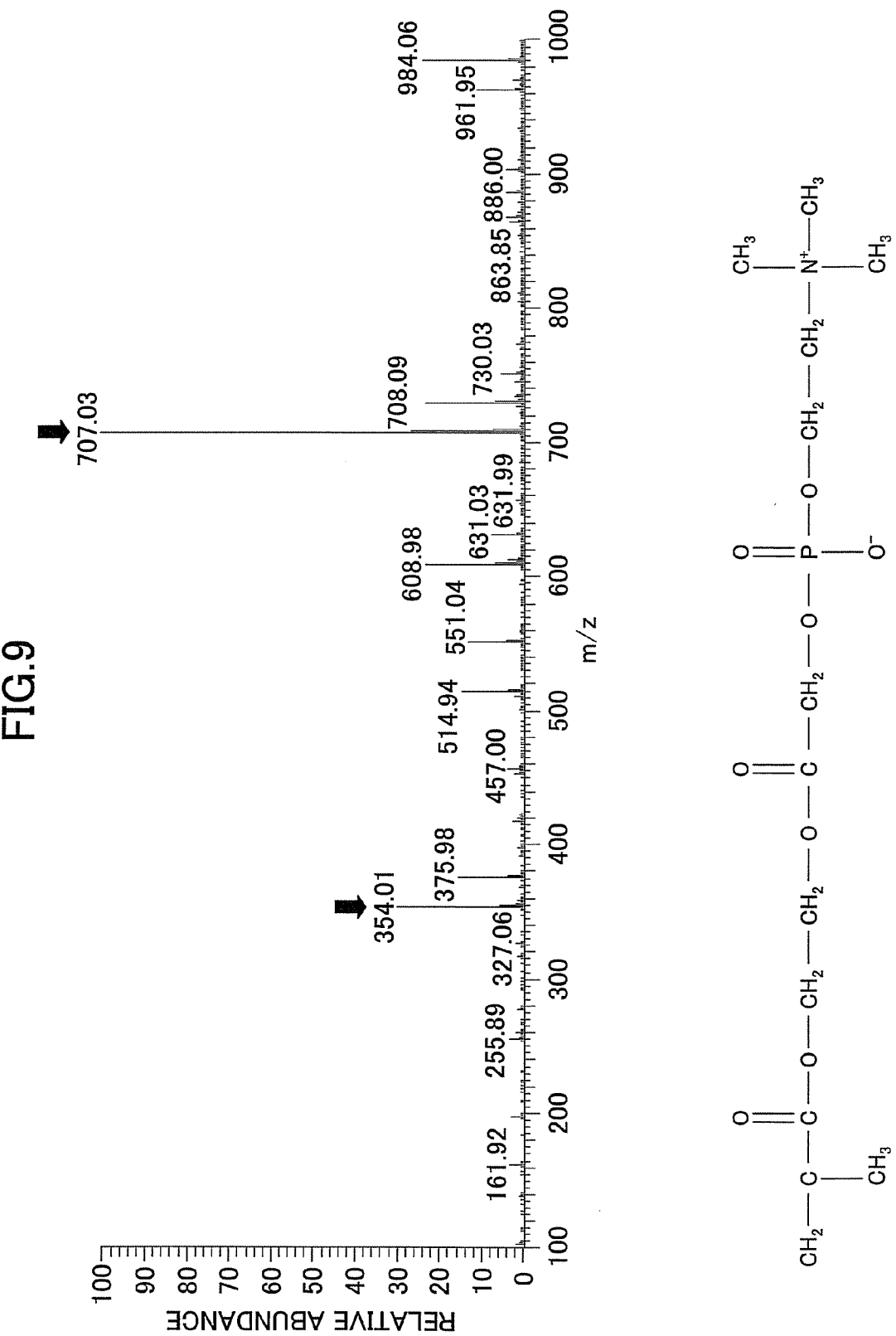
FIG. 9 is a diagram illustrating an MS spectrum of compound E in practical example 4.

(an acrylic compound having a molecular weight of 354 and a phosphorylcholine group) was obtained (see FIG. 8 and FIG. 9). Additionally, it is possible to use compound E as a surface modifying agent similarly to compound B.

Practical Example 5

After ethylenediamine with 20 times equivalent of compound A was added into a solution of compound A in methanol, a triazine-type dehydration condensation agent DMT-MM (produced by Kokusan Chemical Co., Ltd.) with 1.2 times equivalent of compound A was added and agitation was conducted at room temperature for 3 hours to cause reaction. Then, after filtration was conducted to eliminate a precipitate and concentration under a reduced pressure was conducted, drying under a reduced pressure was conducted to obtain compound F represented by a chemical formula of

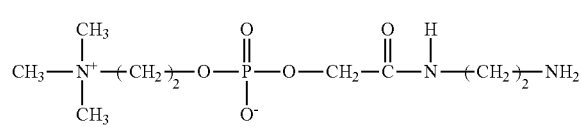

Then, compound F and methacryloyl chloride were added into DMSO and agitation was conducted at room temperature to cause reaction, whereby compound G represented by a chemical formula of

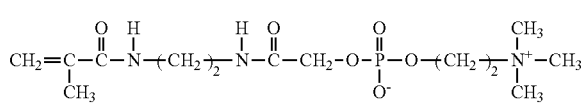

(an acrylic compound having a phosphorylcholine group) was obtained. Additionally, it is possible to use compound G as a surface modifying agent similarly to compound B.

After compound G and butyl methacrylate whose proportion was a molar ratio of 7:3 were added into methanol, 0.05% by mole of ammonium peroxodisulfate $(NH_3)_2S_2O_8$ was added based on the total amount of such monomers and polymerization was conducted at 50° C. for 1 hour, whereby compound H (an acrylic polymer having a phosphorylcholine group) was obtained.

5% by weight solution of compound H in methanol was applied to a 96-well plate made of polystyrene (produced by Becton, Dickinson and Company Japan). Then, after washing with methanol was conducted, drying was conducted to obtain a surface-treated well plate.

Comparative Example 2

After 2-hydroxyethyl methacrylate (HEMA) and butyl methacrylate were added into methanol at a rate of 7:3, 0.05% by mole of ammonium peroxodisulfate $(NH_3)_2S_2O_8$ was added based on the total amount of such monomers and polymerization was conducted at 50° C. for 1 hour, whereby compound I (an acrylic polymer) was obtained.

5% by weight solution of compound I in methanol was applied to a 96-well plate made of polystyrene (produced by Becton, Dickinson and Company Japan). Then, after washing with methanol was conducted, drying was conducted to obtain a surface-treated well plate.

[Protein Adsorption Experiment 3]

Figure 10:
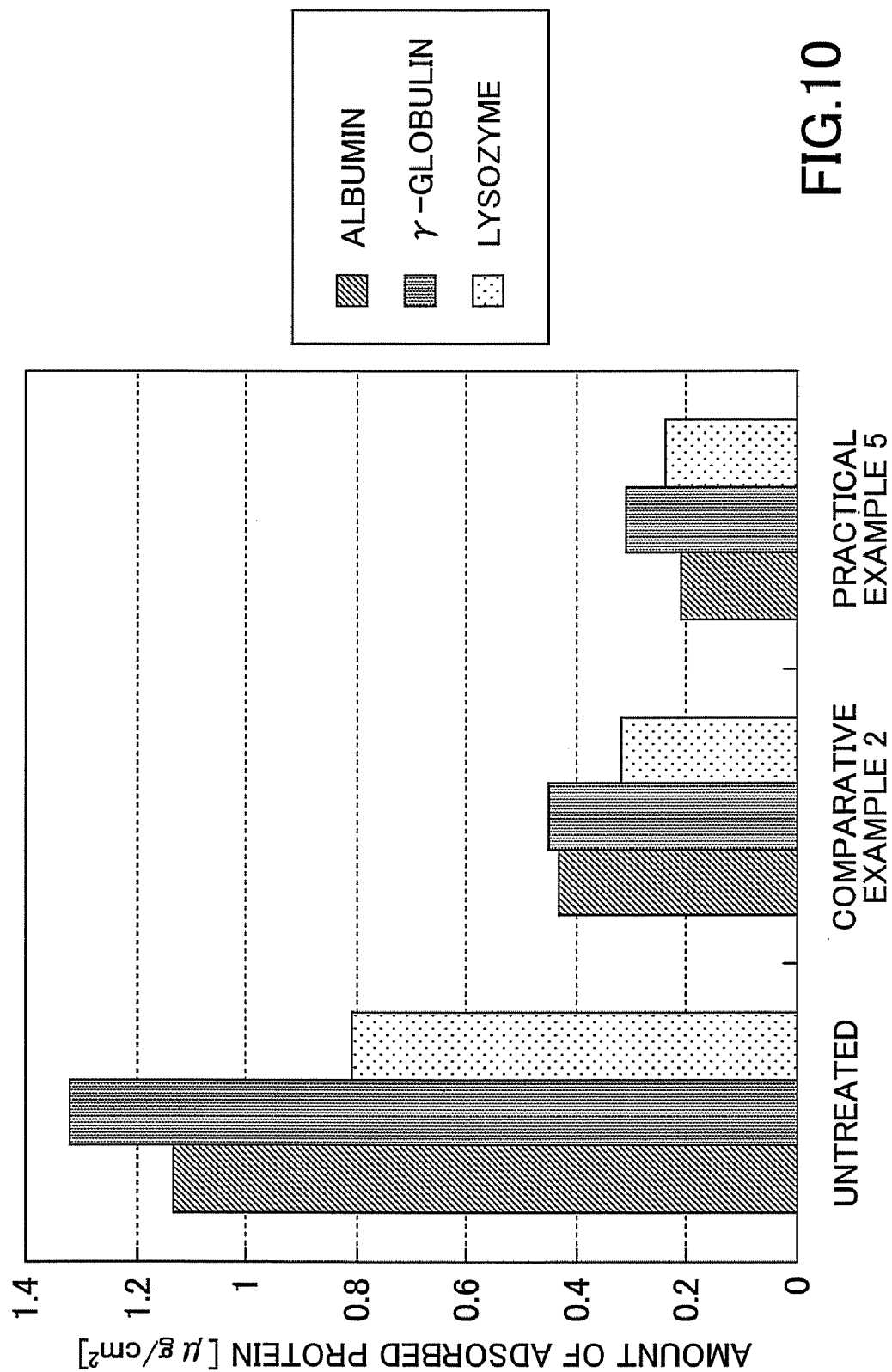
FIG. 10 is a diagram illustrating evaluation results of protein adsorption test 3 in the practical examples.

The amount of an adsorbed protein was quantitatively estimated similarly to protein adsorption experiment 1 except that the surface-treated well plates in practical example 5 and comparative example 2 were used instead of the surface-treated well plate in practical example 1. The evaluation results are illustrated in FIG. 10. It is found from FIG. 10 that it may be possible to control adsorption of any protein of albumin, γ-globulin, and lysozyme to a well plate by conducting the surface treatment. Also, it is found that it may be possible for the surface-treated well plate in practical example 5 to control adsorption of albumin, γ-globulin, and lysozyme better than the surface-treated well plate in comparative example 2.

APPENDIX

At least one embodiment of the present invention aims at providing a polysiloxane having a phosphorylcholine-like group which is capable of controlling a limitation to a pH when used as a surface modifying agent, and a method of manufacturing the polysiloxane. Furthermore, at least one embodiment of the present invention aims at providing a surface modifying agent containing the polysiloxane, and a method of modifying a surface by using the surface modifying agent.

At least one embodiment of the present invention aims at providing an acrylic compound having a phosphorylcholine-like group in which a synthetic method thereof is simple and a hydrolysis resistance thereof is excellent, a method of manufacturing the acrylic compound, and an acrylic polymer obtainable by polymerizing the acrylic compound. Furthermore, at least one embodiment of the present invention aims at providing a surface modifying agent containing the acrylic compound or the acrylic polymer, and a method of modifying a surface by using the surface modifying agent.

At least one embodiment of the present invention aims at providing a vinylic compound having a phosphorylcholine-like group in which a synthetic method thereof is simple and a hydrolysis resistance thereof is excellent, and a method of manufacturing the vinylic compound. Furthermore, at least one embodiment of the present invention aims at providing a surface modifying agent containing the vinylic compound, and a method of modifying a surface by using the surface modifying agent.

The invention as described in embodiment (1) is a polysiloxane characterized by including a structural unit in which a group represented by a general formula of

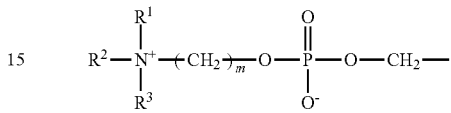

(in the formula, each of $R^1$, $R^2$, and $R^3$ is independently an alkyl group with a carbon number of 1 or more and 6 or less and m is an integer of 2 or more and 6 or less), an ester bond or an amide bond, a spacer, and a silicon atom are bonded sequentially.

The invention as described in embodiment (2) is the polysiloxane as described in embodiment (1), characterized in that the structural unit is represented by a general formula of

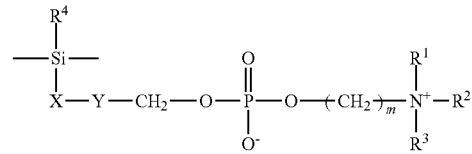

(in the formula, $R^4$ is a hydrogen atom or an alkyl group with a carbon number of 1 or more and 18 or less, X is an alkylene group with a carbon number of 1 or more and 18 or less, a polyoxyalkylene group with a unit number of 1 or more and 18 or less, or an arylene group, and Y is an ester bond or an amide bond).

The invention as described in embodiment (3) is a method of manufacturing the polysiloxane as described in embodiment (1), characterized by including a step of oxidizing glycerophosphorylcholine to synthesize a compound having a carboxyl group or a phosphorylcholine group.

The invention as described in embodiment (4) is a surface modifying agent characterized by containing the polysiloxane as described in embodiment (1).

The invention as described in embodiment (5) is a method of modifying a surface characterized by using the surface modifying agent as described in embodiment (4) to modify a material surface.

The invention as described in embodiment (6) is an acrylic compound characterized in that a group represented by a general formula of

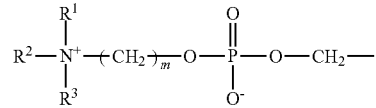

(in the formula, each of $R^1$, $R^2$, and $R^3$ is independently an alkyl group with a carbon number of 1 or more and 6 or less, and m is an integer of 2 or more and 6 or less), an ester bond or an amide bond, a spacer, an ester bond or amide bond, and a group represented by a general formula of

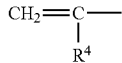

(in the formula, $R^4$ is a hydrogen atom or an alkyl group with a carbon number of 1 or more and 18 or less) are bonded sequentially.

The invention as described in embodiment (7) is the acrylic compound as described in embodiment (6), characterized by being represented by a general formula of

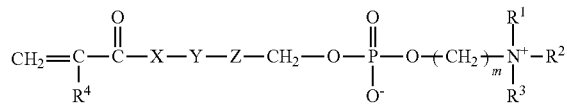

(in the formula, X is an oxy group or an imino group, Y is an alkylene group with a carbon number of 1 or more and 18 or less, a polyoxyalkylene group with a unit number of 1 or more and 18 or less, or an arylene group, and Z is an ester bond or an amide bond).

The invention as described in embodiment (8) is a method of manufacturing the acrylic compound as described in embodiment (6), characterized by including a step of oxidizing glycerophosphorylcholine to synthesize a compound having a carboxyl group and a phosphorylcholine group.

The invention as described in embodiment (9) is a surface modifying agent characterized by containing the acrylic compound as described in embodiment (6).

The invention as described in embodiment (10) is a method of modifying a surface characterized by using the surface modifying agent as described in embodiment (9) to modify a material surface.

The invention as described in embodiment (11) is an acrylic polymer characterized by being a homopolymer or copolymer of the acrylic compound as described in embodiment (6).

The invention as described in embodiment (12) is a surface modifying agent characterized by containing the acrylic polymer as described in embodiment (11).

The invention as described in embodiment (13) is a method of modifying a surface characterized by using the surface modifying agent as described in embodiment (12) to modify a material surface.

The invention as described in embodiment (14) is a vinylic compound characterized in that a group represented by a general formula of

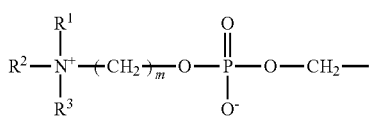

(in the formula, each of $R^1$, $R^2$, and $R^3$ is independently an alkyl group with a carbon number of 1 or more and 6 or less and m is an integer of 2 or more and 6 or less), an ester bond or an amide bond, a spacer, and a group represented by a general formula of

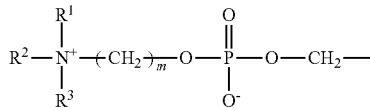

(in the formula, $R^4$ is a hydrogen atom or an alkyl group with a carbon number of 1 or more and 18 or less) are bonded sequentially.

The invention as described in embodiment (15) is the vinylic compound as described in embodiment (14), characterized by being represented by a general formula of

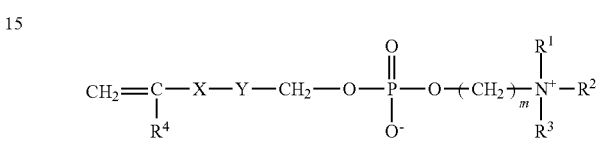

(in the formula, X is an alkylene group with a carbon number of 1 or more and 18 or less, a polyoxyalkylene group with a unit number of 1 or more and 18 or less, or an arylene group, and Y is an ester bond or an amide bond).

The invention as described in embodiment (16) is a method of manufacturing the vinylic compound as described in embodiment (14), characterized by including a step of oxidizing glycerophosphorylcholine to synthesize a compound having a carboxyl group and a phosphorylcholine group.

The invention as described in embodiment (17) is a surface modifying agent characterized by containing the vinylic compound as described in embodiment (14).

The invention as described in embodiment (18) is a method of modifying a surface characterized by using the surface modifying agent as described in embodiment (17) to modify a material surface.

According to at least one embodiment of the present invention, it may be possible to provide a polysiloxane having a phosphorylcholine-like group which is capable of controlling a limitation to a pH when used as a surface modifying agent, and a method of manufacturing the polysiloxane. Furthermore, according to at least one embodiment of the present invention, it may be possible to provide a surface modifying agent containing the polysiloxane, and a method of modifying a surface by using the surface modifying agent.

According to at least one embodiment of the present invention, it may be possible to provide an acrylic compound having a phosphorylcholine-like group in which a synthetic method thereof is simple and a hydrolysis resistance thereof is excellent, a method of manufacturing the acrylic compound, and an acrylic polymer obtainable by polymerizing the acrylic compound. Furthermore, according to at least one embodiment of the present invention, it may be possible to provide a surface modifying agent containing the acrylic compound or the acrylic polymer, and a method of modifying a surface by using the surface modifying agent.

According to at least one embodiment of the present invention, it may be possible to provide a vinylic compound having a phosphorylcholine-like group in which a synthetic method thereof is simple and a hydrolysis resistance thereof is excellent, and a method of manufacturing the vinylic compound. Furthermore, according to at least one embodiment of the present invention, it may be possible to provide a surface modifying agent containing the vinylic compound, and a method of modifying a surface by using the surface modifying agent.

INDUSTRIAL APPLICABILITY

A material modified by a surface modifying agent according to the present invention is a material excellent in biocompatibility and hydrophilicity thereof. Such a material is applicable to a wide variety of applications such as cosmetic materials, medical materials such as artificial organs and tools for a surgical operation, packing materials for chromatography, affinity particles, and coating materials.

The present international application claims the priority based on Japanese Patent Application No. 2008-092762, Japanese Patent Application No. 2008-092763, and Japanese Patent Application No. 20008-092764, filed on Mar. 31, 2008, and the entire contents of Japanese Patent Application No. 2008-092762, Japanese Patent Application No. 2008-092763, and Japanese Patent Application No. 20008-092764 are incorporated by reference in the present international application.

The invention claimed is:

1. A polysiloxane comprising a structural unit having a functional group represented by a general formula of

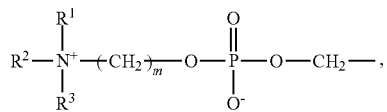

wherein each of $R^1$, $R^2$, and $R^3$ is independently an alkyl group with a carbon number of 1 or more and 6 or less and m is an integer of 2 or more and 6 or less, an ester bond or an amide bond, a spacer, and a silicon atom in sequence.

2. The polysiloxane as claimed in claim 1, wherein the structural unit is represented by a general formula of

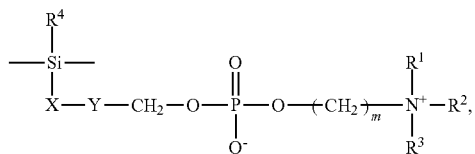

wherein $R^4$ is a hydrogen atom or an alkyl group with a carbon number of 1 or more and 18 or less, X is an alkylene group with a carbon number of 1 or more and 18 or less, a polyoxyalkylene group with a unit number of 1 or more and 18 or less, or an arylene group, and Y is an ester bond or an amide bond.

3. A method of manufacturing the polysiloxane as claimed in claim 1, comprising a step of oxidizing glycerophosphorylcholine to synthesize a compound having a carboxyl group or a phosphorylcholine group.

4. A surface modifying agent containing the polysiloxane as claimed in claim 1.

5. A method of modifying a surface, comprising a step of using the surface modifying agent as claimed in claim 4 to modify a material surface.

* * * * *